United States Patent [19]
Weisker

[11] Patent Number: 5,912,416
[45] Date of Patent: Jun. 15, 1999

[54] SAFFLOWER PRODUCTS WITH VERY HIGH LEVELS OF UNSATURATED FATTY ACIDS

[75] Inventor: Arthur C. Weisker, Woodland, Calif.

[73] Assignee: California Oils Corporation, Richmond, Calif.

[21] Appl. No.: 08/906,368

[22] Filed: Aug. 5, 1997

[51] Int. Cl.$^6$ ................................ A01H 5/00; A01H 5/10; A01H 1/04
[52] U.S. Cl. ................................ 800/298; 800/264; 554/9
[58] Field of Search ..................... 800/200, 205, 800/DIG. 69, 250, 298, 264; 435/172.3; 554/9

[56] References Cited

U.S. PATENT DOCUMENTS

| | | | |
|---|---|---|---|
| 5,276,264 | 1/1994 | Heaton et al. | 800/200 |
| 5,436,386 | 7/1995 | Weisker et al. | 800/200 |
| 5,500,361 | 3/1996 | Kinney | 435/172.3 |
| 5,585,535 | 12/1996 | Fehr et al. | 800/200 |

FOREIGN PATENT DOCUMENTS

WO 9/11906  8/1991  WIPO ............... A01H 1/02

OTHER PUBLICATIONS

Li Dague and Hans Henning Mundel. (1996) *Safflower (Carthamus tincorius L)* pp. 25–35.
Horowitz (1957) *Nature* 179:582–583.
Knowles et al. (1963) *Economic Botany* 17:(2)139–143.
Knowles et al. (Dec. 1965) *California Agriculture*, pp. 15–16.
Applewhite (1966) *The Journal of the American Oil Chemists Society* 43:496–498.
Ladd et al. (1970) *Crop Science* 10:525–527.
Futehally et al. (1981) *Proceedings to the First International Safflower Conference* pp. 56–61.
Vessby (1994) *Inform* 5:182–185.
Mattson et al. (1985) *Journal of Lipid Research* 26:194–202.
Aro et al. (1995) *Lancet* 345:273–277.
Roberts et al. (1995) *Lancet* 345:278–282.
Knowles (1965) *Economic Botany* 19:53–62.
Purdy (1985) *JAOCS* 62:(3)523–525.
Smith (1985) *Safflower*, AOCS Press, chapter 8, pp. 213–253; chapter 9, pp. 254–278; and chapter 15, pp. 365–369.
Knowles et al. (1965) *Crop Science* 4:406–409.
Fernádez–Martinez et al. (1993) *Euphytica* 69:115–122.
Rao (1983) *Indian J. Genet.* 43:68–75.

*Primary Examiner*—Douglas W. Robinson
*Assistant Examiner*—Melissa L. Kimball
*Attorney, Agent, or Firm*—Hale and Dorr LLP

[57] ABSTRACT

The invention is directed to a new safflower line, safflower plants and seeds, and particularly to safflower oil with a fatty acid profile of very high levels of total unsaturated fatty acids compare to the saturated fatty acids content. In particular, this invention is directed to safflower plants and seeds that produce a safflower containing very high levels of oleic acid and reduced levels of linoleic and palmitic acid.

13 Claims, No Drawings

SAFFLOWER PRODUCTS WITH VERY HIGH LEVELS OF UNSATURATED FATTY ACIDS

FIELD OF INVENTION

This invention is in the field of agronomy, specifically plant breeding, more specifically safflower breeding. The invention is directed to a new safflower line, safflower plants and seeds, and particularly to safflower oil with a fatty acid profile of very high levels of total unsaturated fatty acids compared to the saturated fatty acids content. In particular, this invention is directed to safflower plants and seeds that produce a safflower containing very high levels of oleic acid and reduced levels of linoleic and palmitic acid.

BACKGROUND OF THE INVENTION

Safflower (*Carthamus tinctorius* l) is a member of the compositae family. Safflower was first cultivated in the Near East thousands of years ago as a source of dye and other products that can be derived from the plant. (Li and Mundell, *Safflower* (*Carthamus tincorius* l), IPGRI No. 7, 1996). Safflower in this century has been utilized as a source of edible oils. Safflower was introduced to agriculture in the United States in the 1930's. With the introduction of varieties with improved oil content in the 1950's, safflower found a niche in the agricultural system. Safflower is primarily grown in the Central Valley of California, and to a lesser extent, in the Northern Plains States.

The original cultivars of safflower contained high levels of linoleic acid. Indeed, safflower has higher linoleic acid levels than any other oilseed crop grown commercially. These varieties also have the highest ratio of unsaturated to saturated fats compared to other oilseed crops. (Li and Mundell, supra, 1996.) In the 1950's, an oleic variant of safflower was first described by Horowitz (Horowitz, "A New Safflower Oil with a Low Iodine Value," *Nature*, 179:582,583, 1957). This variant was genetically described in 1963 by Knowles and Mutwakil (Knowles, P. F. and Mutwakil, A., "Inheritance of Low Iodine Value of Safflower Selections from India," *Economic Botany*, 17(2):139–143, 1963). Subsequent breeding resulted in the release of UC1, an oleic variety of safflower (Knowles, Hill and Ruckman, "High Oleic Acid Content in New Safflower UC-1," *California Agriculture*, pp. 15–16, December, 1965). Oleic safflower varieties were subsequently released commercially, and in recent years have come to dominate the safflower market. The release of oleic safflower types marked the first time that one species was represented by varieties differing substantially in fatty acid type. Later discoveries accented the variability present in the safflower gene pool. Most notably a high stearic line (Ladd and Knowles, "Inheritance of Stearic Acid in the Seed Oil of Safflower (*Carthamus tinctorius* L.)," *Crop Science*, 10:525–527, September–October 1970) and a very high linoleic line (Futehally and Knowles, "inheritance of Very High Levels of Linoleic Acid in an Introduction of Safflower (*Carthamus tinctorius* L) from Portugal," *Proceedings of the First International Safflower Conference*, pp.56–61, 1981) were described. This variability has opened the possibility of creating new safflower varieties with unique fatty acid profiles for edible and industrial uses.

Safflower oil primarily comprises the fatty acids palmitic, stearic, oleic, and linoleic acids: palmitic ($C16:0$) and stearic acids ($C18:0$) are saturated fatty acids; oleic ($C18:1$) and linoleic ($C18:2$) are unsaturated fatty acids.

Numerous health studies have been conducted in recent years linking the types of fats consumed to health issues, especially cholesterol levels. It has been recognized that unsaturated fatty acids have superior health benefits compared to saturated fatty acids, especially those containing fewer than eighteen carbon atoms. Saturated fats with eighteen or more carbon atoms seem to have little or no effect on cholesterol levels (Vessby, "Implications of Long-Chain Fatty Acid Studies," *INFORM*, pp. 182–185. 1994).

Recent studies regarding fatty acids and health issues, especially heart disease, indicate an advantage of oleic acid over other vegetable oil fatty acids, or at least fewer disadvantages than such fatty acids. There have been conflicting results among studies, but two recent findings are noteworthy. It has been found that oleic acid is superior to linoleic acid regarding cholesterol level and levels of HDL (Mattson and Grundy, "Comparison of effects of Dietary Saturated, Monounsaturated, and Polyunsaturated Fatty Acids on Plasma Lipids and Lipoproteins in Man, *Journal of Lipid Research*, 26:194–202, 1985). Trans fatty acids, created through hydrogenization of unsaturated fatty acids, have the effect of elevating cholesterol levels. Recent studies (Aro et. al., "Adipose Tissue Isomeric Trans Fatty Acids and Risk of Myocardial Infarction in Nine Countries: the EURAMIC Study," *Lancet*, 345:273–278, 1995; and Roberts et al., "Trans Isomers of Oleic and Linoleic Acids in Adipose Tissue and Sudden Cardiac Death, *Lancet*, 345:278–282, 1995) indicate that trans-oleic acid may have fewer health problems than originally thought and that it may be less detrimental than trans-linoleic acid.

From a health standpoint, a vegetable oil with increased oleic acid as well as decreased palmitic acid would be highly desirable. Since palmitic acid is the only saturated fat with fewer than eighteen carbon atoms found in safflower in significant amounts, a safflower variety with decreased palmitic acid and increased oleic acid would be highly desirable.

Higher oleic acid levels also have potential for industrial uses. Increases in oleic acid are highly correlated with lower levels of linoleic acid (Knowles, "Variability in Oleic and Linoleic Acid Contents of Safflower Oil" *Economic Botany*, 19:53–62, 1965). Low levels of linoleic acid correlate positively with oil stability (Purdy, "Oxidative Stability of High Oleic Sunflower and Safflower" *JAOCS*, 62(3):523–525, 1985). Highly stable oils have uses in a number of markets. Manufacturers use oleic acid for infant formula and food supplements due to the greater shelf life of the oil. Oils with greater stability are being sought as an agent in spray-on flavor additives. If the oleic acid level could reach or exceed 90% additional markets would be available. Included in these markets are artificial coconut butter substitutes which attempt to duplicate cocoa butter, and in pharmaceutical and industrial creation of pure oleic acid. This process is currently done using inexpensive oils low in oleic acid. Oleic acid levels in the 90% range would make a more cost efficient means of purifying the oil. A number of other industrial uses for oleic safflower have been proposed and tested. A safflower variety with increased oleic acid and decreased linoleic acid may be superior to current oleic types for use in any of these projects. A complete summary of industrial oil uses can be found in the 5 volume book Bailey's Industrial Oil & Fats Products. A summary of industrial uses for safflower oil is given in Chapters 8, 9, and part of 15 of SAFFLOWER (Smith, "Safflower," AOCS Press, Chapters 8, 9, 15. pp. 254–260, 365–369. 1996).

SUMMARY OF THE INVENTION

This invention is directed to safflower seeds derived from a safflower line with a gene that controls high levels of oleic acid content of the fatty acid profile in the oil from said seeds, wherein the total unsaturated fatty acid oil content in said seeds is greater than about 92% of the total oil content and wherein the ratio of linoleic acid to oleic acid is less than 0.03.

This invention is further directed to safflower seeds comprising a fatty acid profile of total unsaturated fatty acids greater than about 92%, preferably greater than about 93%, more preferably greater than about 94% of the total oil content, wherein the ratio of linoleic acid to oleic acid is less than 0.03.

This invention is also directed to safflower seeds comprising a fatty acid profile which comprises an oleic acid content greater than about 90%, preferably greater than about 91%, linoleic acid content of about 3% or less, palmitic acid content of less than about 4%, and stearic acid content of about 2.5% or less.

This invention is also directed to a safflower plant that has a trait inherited from safflower line S-901 or a plant derived from safflower line S-901, such that said safflower plant yields bulked seed that provides oil wherein the total unsaturated fatty acid oil content of said seed is greater than about 92% of the total oil content and wherein the ratio of linoleic to oleic acid is less than 0.03. The invention further comprises a safflower plant derived from the seed of such safflower plant.

This invention is directed to a method of producing seeds with at least about 90% oleic acid content from a safflower plant and to a method of producing safflower oil from a safflower seed with an oleic acid content of at least about 90%.

This invention is further directed to a safflower oil having an oleic add content of at least about 90% and a linoleic acid content of less than 3%, relative to the total fatty acid content of said oil.

DETAILED DESCRIPTION OF THE INVENTION

The present invention is directed to a safflower line where the oil from the safflower seeds has a unique fatty acid profile: the oil has very high total unsaturated fatty acids and very low saturated fatty acids, with the ratio of linoleic acid to oleic acid being less than 0.03. In particular, this safflower line produces seeds with oil that have increased oleic acid content and decreased palmitic acid. In addition, this safflower line produces seeds with oil with low levels of linoleic acid. This invention is thus also directed to the safflower oil with this fatty acid profile and, due to the low linoleic acid content and the very high oleic acid content, is highly stable. This invention is further directed to methods of growing a safflower plant to produce safflower oil with the fatty acid profile and to methods of producing the safflower oil with the fatty acid profile from the safflower seed. Additionally, the invention includes safflower plants, seeds, and plant parts with the phenotypic, physiological, and morphologic characteristics of safflower line designated S-901. This safflower line has a generally broad based combining ability with other safflower lines to produce the desired characteristics in combination.

According to this invention, the safflower line's unique fatty acid profile is as follows: Total unsaturated fatty acids range from about 92.8 to about 94.3% of total oil content, with the ratio of linoleic acid to oleic acid being less than 0.03. Total saturated fatty acids range from about 5.7 to about 7.2% of total oil content. This safflower line has an oleic acid content with an average of greater than 90%, preferably greater than 91%. Linoleic acid content ranges from about 2.0% to about 2.7%, with the average of about 2.3%. Palmitic acid content ranges from about 3.5 to about 4.1%, with the average of about 3.8%. Stearic acid content ranges from about 1.3% to about 2.2%, with the average of about 1.8%.

In accordance with the present invention, safflower line is characterized by safflower seeds with a oil that has a fatty acid profile of total unsaturated fatty acids greater than 92% of the total oil content, preferably greater than 93%, more preferably greater than 94%, with the ratio of linoleic acid to oleic acid being less than 0.03.

The safflower seeds of the invention are further characterized by an oil that has a fatty acid profile of an oleic acid content greater than about 90%, linoleic acid content of about 3% or less, palmitic acid content of less than about 4%, and stearic acid content of about 2.5% or less. Preferably, the safflower seeds of the invention are characterized by an oil that has a fatty acid profile of an oleic acid content greater than about 91%, linoleic acid content of about 2.5% or less, palmitic acid content of less than about 4%, and stearic acid content of about 2.5% or less.

Once the seed is harvested, the oil from the safflower seed can be extracted, typically by crushing the seed, and then refined using any conventional method. The safflower oil of this invention is characterized by an oleic acid content of at least about 90% and a linoleic acid content of less than 3%, relative to the total fatty acid content of the oil.

A single gene has been identified that, when homozygous in a plant, described above controls the fatty acid profile of the safflower line. Plants from this line are able to be cross-pollinated to other safflower lines to create new lines with the same fatty acid profile as well as new lines with different fatty acid profiles to derive the desired fatty acid profile useful for commercial and industrial purposes.

As used herein, the terms, "line", "cultivar", and "variety", are used interchangeably and refer to a group of plants which are uniform in their traits such that there is relatively minor variation within the group.

As used herein, the terms "plant and plant parts" include plant cells, plant protoplasts, plant cell tissue culture from which safflower plants can be regenerated, plant calli, plant clumps, and plant cells that are intact in plants or parts of plants, such as embryos, pollen, flowers, leaves, stalks, roots, root tips, anthers, and the like. Plant tissue culture procedures are described in *Plant Cell Culture,* IRL Press, R. A. Dixon, editor, 1991. Thus, another aspect of this invention is to provide cells which upon growth and differentiation produce the safflower line S-901.

Growth under climatic conditions that are cooler or warmer may result in a somewhat altered fatty acid composition of the safflower line. However, while the specific results may vary somewhat depending upon the specific growing conditions, the progeny of the invention will be characterized by very high oleic acid content and very high total unsaturated fatty acid profile. The present invention has a very low level of saturated fatty acid in the oil. The safflower oil of this invention is thus highly stable, that is, it is not as susceptible to oxidative deterioration.

The fatty acid composition is typically determined by gas chromatography using the method as generally outlined in Graef et al., *Crop Sci.,* 25:1076–1079 (1985). In general, this method involves the steps of (1) crushing the seed sample; (2) putting the crushed sample into a test tube with heptane solvent and extracting the oil into the heptane; (3) the fatty acids in the oil are converted to their methyl esters using sodium methoxide and methanol; (4) water is added to inactivate the sodium methoxide catalyst, and (5) the methyl esters, which float to the top of the water layer, are dilute with heptane and become the sample that is introduced into the column of the gas chromatography apparatus.

The novel safflower seeds and plants of the present invention, characterized by very high levels of oleic acid and reduced levels of palmitic acid, and linoleic acid were the result of a mutation breeding program. The safflower line resulting from the continued breeding program has been given the name S-901. The source seed was commercial available oleic variety S-518. S-518 is a high yielding safflower variety with an oleic content higher than most commercial lines. Two pounds of S-518 seed was treated using 0.5% ethyl mecuric sulfonanilide (EMS), a known mutagenic agent. After treatment, the wet seed was planted in three breeding cages, each of which plants 1500 square feet. Lethality in the M1 generation was high: at the end of the season about one pound of M2 seed was bulk harvested. Over each of the next three years, one third of the M2 seed was replanted into a single breeding cage. M2 plants were individually harvested and gas chromatograph (GC) analysis was performed.

M3 lines with fatty acid profiles that appeared potentially unique were grown in nursery rows for further analysis. One particularly intriguing line had an oleic acid level of 85%. This selection was grown in a small breeding cage to insure self pollination of all plants. Individual plants were harvested and the fatty acids profile determined. Table 1 shows the oleic acid contents of the 168 M3 plants analyzed.

TABLE 1

OLEIC ACID CONCENTRATION OF SEGREGANTS OF S-901 OBSERVED AND EXPECTED RATIOS FOR 1:2:1 SEGREGATION

| | | OLEIC ACID CONCENTRATION | | | |
|---|---|---|---|---|---|
| | | 89.5–91.5% | 81.5–88.5% | 77.7–51.5% | CHI-SQ. |
| S-901 M3 PLANTS | OBS | 21 | 96 | 51 | 14.1** |
| | EXP | 42 | 84 | 42 | |
| S-901 × S-518: F2 SEED | OBS | 5 | 25 | 10 | 3.75 |
| | EXP | 10 | 20 | 10 | |
| 8-901 × 6115: F2 SEED | OBS | 10 | 22 | 7 | 1.09 |
| | EXP | 9.7 | 19.5 | 9.7 | |
| F2 COMBINED | OBS | 15 | 47 | 17 | 2.94 |
| | EXP | 19.7 | 39.4 | 19.7 | |

This ratio was not the classic 1:2:1 ratio of a single recessive gene due to the low number of plants showing the 90% mutation. Subsequent observations have shown a lower survival rate in the 90% line which can explain the observed ratio. Tests using single seed analysis have provided clear 1:2:1 ratios as expected for a single recessive gene (Table 1).

Table 2 shows the fatty acid profile of thirty nine F2 seed of the cross S-901 x6115, a proprietary safflower line. Based on this fatty acid profile, it is evident that the mutation has its effect on the palmitic and linoleic acids as well as oleic acid.

TABLE 2

FATTY ACID PROFILE OF F2 SEED OF THE CROSS S-901 × 6115

| SEED NO. | | 16:0 | 18:0 | 18:1 | 18:2 |
|---|---|---|---|---|---|
| 1 | | 3.5 | 1.5 | 91.2 | 2.3 |
| 2 | | 3.3 | 1.6 | 91.2 | 2.3 |
| 3 | | 3.6 | 1.6 | 91.0 | 2.2 |
| 4 | | 3.7 | 1.7 | 90.8 | 2.4 |
| 5 | | 3.7 | 1.6 | 90.8 | 1.9 |
| 6 | | 3.6 | 1.7 | 90.7 | 2.3 |
| 7 | | 3.6 | 1.6 | 90.6 | 2.3 |
| 8 | | 3.8 | 1.7 | 90.5 | 2.2 |
| 9 | | 3.6 | 2.1 | 90.3 | 2.2 |
| 10 | | 3.8 | 1.6 | 90.2 | 2.3 |
| 11 | | 3.9 | 1.6 | 85.8 | 7.0 |
| 12 | | 4.4 | 1.6 | 85.7 | 6.7 |
| 13 | | 4.1 | 1.5 | 85.3 | 7.5 |
| 14 | | 4.2 | 1.8 | 85.2 | 6.8 |
| 15 | | 4.2 | 1.6 | 85.1 | 7.5 |
| 16 | | 4.5 | 1.6 | 84.9 | 7.5 |
| 17 | | 4.3 | 1.7 | 84.9 | 7.0 |
| 18 | | 4.2 | 1.7 | 84.8 | 7.4 |
| 19 | | 4.5 | 1.7 | 84.7 | 7.0 |
| 20 | | 4.5 | 1.7 | 84.6 | 7.7 |
| 21 | | 4.2 | 1.7 | 84.5 | 7.5 |
| 22 | | 4.2 | 1.7 | 84.4 | 7.9 |
| 23 | | 4.2 | 1.6 | 84.4 | 8.1 |
| 24 | | 4.3 | 1.6 | 84.3 | 8.1 |
| 25 | | 4.2 | 1.7 | 84.3 | 7.4 |
| 26 | | 4.3 | 1.8 | 84.2 | 7.5 |
| 27 | | 4.4 | 1.6 | 84.1 | 8.2 |
| 28 | | 4.4 | 1.6 | 83.9 | 8.2 |
| 29 | | 4.6 | 1.5 | 83.6 | 8.7 |
| 30 | | 4.3 | 1.5 | 83.5 | 8.7 |
| 31 | | 4.5 | 1.6 | 83.1 | 8.8 |
| 32 | | 4.4 | 1.6 | 82.9 | 9.3 |
| 33 | | 4.8 | 1.6 | 80.3 | 12.0 |
| 34 | | 4.4 | 1.8 | 80.3 | 11.3 |
| 35 | | 4.5 | 2.0 | 80.1 | 11.8 |
| 36 | | 4.9 | 1.8 | 79.6 | 12.0 |
| 37 | | 4.8 | 1.7 | 79.3 | 11.9 |
| 38 | | 4.6 | 1.6 | 78.9 | 13.1 |
| 39 | | 4.9 | 1.7 | 78.2 | 13.5 |
| S-901 TYPE | AVG | 3.6 | 1.7 | 90.7 | 2.2 |
| N = 10 | STD | 0.15 | 0.15 | 0.33 | 0.12 |
| HETEROZYGOUS TYPE | AVG | 4.3 | 1.6 | 84.5 | 7.8 |
| N = 22 | STD | 0.16 | 0.08 | 0.74 | 0.69 |
| NORMAL TYPE | AVG | 4.7 | 1.7 | 79.5 | 12.2 |
| N = 7 | STD | 0.17 | 0.14 | 0.74 | 0.74 |

M4 plants with the 90% trait were grown the following generation to confirm the nature of the new gene. Crosses and backcrosses were initiated at the same time to begin creating improved genotypes containing the 90% trait. The results of the M5 generation confirmed that the trait was fixed and reproducible (Table 3).

TABLE 3

COMPARISON OF M4 AND M5 SELECTIONS OF S-901

| VARIETY | | 16:0 | 18:0 | 18:1 | 18:2 | TOT SAT* |
|---|---|---|---|---|---|---|
| 518M-23-6 | M4 SELECTION | 3.7 | 1.8 | 90.4 | 2.3 | 6.5 |
| 518M-23-6 | AVG OF 5 M5 PLANTS | 3.6 | 1.8 | 90.9 | 2.2 | 6.4 |
| 518M-23-8 | M4 SELECTION | 3.7 | 1.8 | 90.1 | 2.5 | 6.6 |
| 518M-23-8 | AVG OF 5 M5 PLANTS | 3.8 | 1.8 | 89.8 | 3.1 | 6.6 |
| 518M-23-11 | M4 SELECTION | 3.7 | 1.9 | 90.3 | 2.3 | 6.6 |
| 518M-23-11 | AVG OF 5 M5 PLANTS | 3.7 | 1.8 | 90.7 | 2.2 | 6.7 |
| 518M-23-12 | M4 SELECTION | 3.6 | 1.8 | 90.5 | 2.2 | 6.5 |
| 518M-23-12 | AVG OF 5 M5 | 3.8 | 1.7 | 86.5 | 6.5 | 6.5 |

TABLE 3-continued

COMPARISON OF M4 AND M5 SELECTIONS OF S-901

| VARIETY | | 16:0 | 18:0 | 18:1 | 18:2 | TOT SAT* |
|---|---|---|---|---|---|---|
| 518M-23-17 | M4 SELECTION PLANTS | 3.7 | 2.0 | 90.2 | 2.3 | 6.8 |
| 518M-23-17 | AVG OF 5 M5 PLANTS | 3.6 | 1.9 | 91.0 | 2.1 | 6.4 |
| 518M-23-19 | M4 SELECTION | 3.7 | 1.7 | 90.4 | 2.3 | 6.4 |
| 518M-23-19 | AVG OF 5 M5 PLANTS | 3.8 | 1.8 | 90.9 | 2.2 | 6.5 |
| 518M-23-20 | M4 SELECTION | 3.6 | 1.7 | 90.5 | 2.3 | 6.3 |
| 518M-23-20 | AVG OF 5 M5 PLANTS | 3.8 | 1.8 | 91.0 | 2.0 | 6.5 |

*TOTAL SATURATED FAT EQUALS SUM OF ALL SATURATED FATS 14:0–24:0

Selections in the M5 generations were again grown and bulk samples of M6 rows were analyzed for fatty acid type. The results are shown in Table 4.

TABLE 4

COMPARISON OF M5 AND M6 SELECTIONS OF S-901

| VARIETY | | 14:0 | 16:0 | 18:0 | 18:1 | 18:2 | 20:0 | 22:0 | 24:0 | TOT SAT |
|---|---|---|---|---|---|---|---|---|---|---|
| 518M-23-6-1 | M5 SELECTION | 0.1 | 3.6 | 1.7 | 91.0 | 2.2 | 0.4 | 0.4 | 0.1 | 6.3 |
| 518M-23-6-1 | M6 BULK | 0.0 | 3.7 | 1.8 | 90.2 | 2.3 | 0.5 | 0.4 | 0.2 | 6.6 |
| 518M-23-6-2 | M5 SELECTION | 0.2 | 3.7 | 1.8 | 90.7 | 2.2 | 0.4 | 0.4 | 0.1 | 6.7 |
| 518M-23-6-2 | M6 BULK | 0.0 | 3.8 | 1.9 | 90.0 | 2.4 | 0.5 | 0.4 | 0.2 | 6.8 |
| 518M-23-6-3 | M5 SELECTION | 0.0 | 3.7 | 1.8 | 91.1 | 2.1 | 0.4 | 0.4 | 0.1 | 6.4 |
| 518M-23-6-3 | M6 BULK | 0.0 | 3.8 | 2.0 | 90.1 | 2.3 | 0.5 | 0.4 | 0.2 | 6.8 |
| 518M-23-6-4 | M5 SELECTION | 0.2 | 3.6 | 1.9 | 90.8 | 2.2 | 0.5 | 0.4 | 0.1 | 6.6 |
| 518M-23-6-4 | M6 BULK | 0.0 | 3.7 | 1.8 | 90.1 | 2.5 | 0.4 | 0.4 | 0.2 | 6.5 |
| 518M-23-6-5 | M5 SELECTION | 0.2 | 3.7 | 1.9 | 90.7 | 2.2 | 0.4 | 0.4 | 0.1 | 6.6 |
| 518M-23-6-5 | M6 BULK | 0.0 | 3.8 | 2.0 | 90.1 | 2.3 | 0.5 | 0.4 | 0.2 | 6.9 |
| 518M-23-8-1 | M5 SELECTION | 0.1 | 3.6 | 1.9 | 91.0 | 2.0 | 0.4 | 0.4 | 0.1 | 6.5 |
| 518M-23-8-1 | M6 BULK | 0.0 | 4.1 | 1.9 | 79.3 | 12.9 | 0.4 | 0.4 | 0.2 | 7.0 |
| 518M-23-8-2 | M5 SELECTION | 0.2 | 3.8 | 1.8 | 90.8 | 2.1 | 0.4 | 0.4 | 0.1 | 6.6 |
| 518M-23-8-2 | M6 BULK | 0.0 | 3.7 | 1.9 | 90.2 | 2.3 | 0.4 | 0.4 | 0.2 | 6.7 |
| 518M-23-8-3 | M5 SELECTION | 0.2 | 3.8 | 1.7 | 90.8 | 2.1 | 0.4 | 0.4 | 0.1 | 6.6 |
| 518M-23-8-3 | M6 BULK | 0 | 3.93 | 1.94 | 90.2 | 2.11 | 0.44 | 0.40 | 0.17 | 6.8 |
| 518M-23-8-4 | M5 SELECTION | 0.1 | 3.6 | 1.8 | 91.1 | 2.0 | 0.4 | 0.4 | 0.1 | 6.4 |
| 518M-23-8-4 | M6 BULK | 0.0 | 4.0 | 2.0 | 74.7 | 7.6 | 0.4 | 0.4 | 2.0 | 7.0 |
| 518M-23-11-1 | M5 SELECTION | 0.2 | 3.7 | 1.8 | 90.8 | 2.0 | 0.4 | 0.4 | 0.1 | 6.6 |
| 518M-23-11-1 | M6 BULK | 0.0 | 3.7 | 1.8 | 90.2 | 2.3 | 0.4 | 0.4 | 0.2 | 6.6 |
| 518M-23-11-2 | M5 SELECTION | 0.2 | 3.7 | 1.9 | 90.4 | 2.2 | 0.5 | 0.4 | 0.1 | 6.8 |
| 518M-23-11-2 | M6 BULK | 0.0 | 3.8 | 1.9 | 90.1 | 2.2 | 0.5 | 0.4 | 0.2 | 6.8 |
| 518M-23-11-3 | M5 SELECTION | 0.2 | 3.7 | 1.7 | 90.9 | 2.2 | 0.4 | 0.4 | 0.1 | 6.5 |
| 518M-23-11-3 | M6 BULK | 0.0 | 3.8 | 1.8 | 89.9 | 2.4 | 0.4 | 0.4 | 0.2 | 6.7 |
| 518M-23-11-4 | M5 SELECTION | 0.0 | 3.7 | 1.8 | 90.8 | 2.3 | 0.5 | 0.4 | 0.1 | 6.5 |
| 518M-23-11-4 | M6 BULK | 0.0 | 3.7 | 1.9 | 90.0 | 2.4 | 0.5 | 0.4 | 0.2 | 6.8 |
| 518M-23-11-5 | M5 SELECTION | 0.2 | 3.6 | 1.7 | 91.1 | 2.2 | 0.4 | 0.4 | 0.1 | 6.3 |
| 518M-23-11-5 | M6 BULK | 0.0 | 3.8 | 1.9 | 90.1 | 2.3 | 0.5 | 0.4 | 0.2 | 6.8 |
| 518M-23-11-6 | M5 SELECTION | 0.3 | 3.9 | 2.1 | 90.2 | 2.3 | 0.5 | 0.4 | 0.1 | 7.3 |
| 518M-23-11-6 | M6 BULK | 0.0 | 3.7 | 1.7 | 90.3 | 2.4 | 0.4 | 0.4 | 0.2 | 6.4 |
| 518M-23-17-1 | M5 SELECTION | 0.0 | 3.8 | 2.0 | 90.8 | 2.0 | 0.5 | 0.4 | 0.1 | 6.7 |
| 518M-23-17-1 | M6 BULK | 0.0 | 3.8 | 2.0 | 90.2 | 2.1 | 0.5 | 0.4 | 0.2 | 6.8 |
| 518M-23-17-2 | M5 SELECTION | 0.0 | 3.5 | 1.8 | 91.1 | 2.1 | 0.5 | 0.4 | 0.1 | 6.2 |
| 518M-23-17-2 | M6 BULK | 0.0 | 3.7 | 1.7 | 90.2 | 2.5 | 0.4 | 0.4 | 0.2 | 6.4 |
| 518M-23-17-3 | M5 SELECTION | 0.0 | 3.7 | 1.8 | 91.0 | 2.1 | 0.4 | 0.4 | 0.1 | 6.4 |
| 518M-23-17-3 | M6 BULK | 0.0 | 3.7 | 1.7 | 90.4 | 2.2 | 0.4 | 0.4 | 0.2 | 6.5 |
| 518M-23-17-4 | M5 SELECTION | 0.0 | 3.6 | 1.9 | 90.9 | 2.3 | 0.5 | 0.4 | 0.1 | 6.5 |
| 518M-23-17-4 | M6 BULK | 0.0 | 3.7 | 1.7 | 90.2 | 2.3 | 0.4 | 0.4 | 0.2 | 6.5 |
| 518M-23-17-5 | M5 SELECTION | 0.0 | 3.6 | 1.7 | 91.3 | 2.0 | 0.4 | 0.4 | 0.1 | 6.2 |
| 518M-23-17-5 | M6 BULK | 0.0 | 3.7 | 1.7 | 90.3 | 2.3 | 0.4 | 0.4 | 0.2 | 6.4 |
| 518M-23-19-1 | M5 SELECTION | 0.2 | 3.7 | 1.7 | 90.9 | 2.2 | 0.4 | 0.4 | 0.1 | 6.5 |
| 518M-23-19-1 | M6 BULK | 0.0 | 4.2 | 2.1 | 81.4 | 10.5 | 0.5 | 0.4 | 0.2 | 7.3 |
| 518M-23-19-2 | M5 SELECTION | 0.0 | 3.5 | 1.6 | 91.4 | 2.2 | 0.4 | 0.4 | 0.1 | 6.0 |
| 518M-23-19-2 | M6 BULK | 0.0 | 3.8 | 1.9 | 90.3 | 2.1 | 0.5 | 0.4 | 0.2 | 6.8 |
| 518M-23-19-3 | M5 SELECTION | 0.0 | 3.9 | 1.8 | 90.8 | 2.1 | 0.4 | 0.4 | 0.1 | 6.6 |
| 518M-23-19-3 | M6 BULK | 0.0 | 3.8 | 1.8 | 90.2 | 2.2 | 0.4 | 0.4 | 0.2 | 6.7 |
| 518M-23-19-4 | M5 SELECTION | 0.0 | 3.9 | 1.8 | 90.8 | 2.1 | 0.4 | 0.4 | 0.1 | 6.7 |
| 518M-23-19-4 | M6 BULK | 0.0 | 3.9 | 1.8 | 90.1 | 2.2 | 0.4 | 0.4 | 0.2 | 6.8 |
| 518M-23-19-5 | M5 SELECTION | 0.0 | 3.9 | 1.7 | 90.8 | 2.2 | 0.4 | 0.4 | 0.1 | 6.5 |
| 518M-23-19-5 | M6 BULK | 0.0 | 3.8 | 1.9 | 90.2 | 2.1 | 0.5 | 0.4 | 0.2 | 6.9 |
| 518M-23-20-1 | M5 SELECTION | 0.0 | 3.8 | 1.7 | 91.1 | 2.1 | 0.4 | 0.4 | 0.1 | 6.4 |
| 518M-23-20-1 | M6 BULK | 0.0 | 3.7 | 1.8 | 90.4 | 2.2 | 0.4 | 0.4 | 0.2 | 6.5 |

TABLE 4-continued

COMPARISON OF M5 AND M6 SELECTIONS OF S-901

| VARIETY | | 14:0 | 16:0 | 18:0 | 18:1 | 18:2 | 20:0 | 22:0 | 24:0 | TOT SAT |
|---|---|---|---|---|---|---|---|---|---|---|
| 518M-23-20-2 | M5 SELECTION | 0.0 | 3.8 | 1.9 | 90.8 | 2.1 | 0.4 | 0.4 | 0.1 | 6.6 |
| 518M-23-20-2 | M6 BULK | 0.0 | 3.7 | 1.7 | 90.3 | 2.4 | 0.4 | 0.4 | 0.2 | 6.4 |
| 518M-23-20-3 | M5 SELECTION | 0.0 | 3.8 | 1.8 | 91.0 | 2.0 | 0.4 | 0.4 | 0.1 | 6.6 |
| 518M-23-20-3 | M6 BULK | 0.0 | 3.9 | 1.8 | 90.1 | 2.3 | 0.4 | 0.4 | 0.2 | 6.7 |
| 518M-23-20-4 | M5 SELECTION | 0.0 | 3.9 | 1.9 | 90.9 | 2.0 | 0.4 | 0.4 | 0.1 | 6.7 |
| 518M-23-20-4 | M6 BULK | 0.0 | 3.8 | 1.7 | 90.3 | 2.3 | 0.4 | 0.4 | 0.2 | 6.6 |
| 518M-23-20-5 | M5 SELECTION | 0.0 | 3.6 | 1.8 | 91.2 | 2.1 | 0.4 | 0.4 | 0.1 | 6.3 |
| 518M-23-20-5 | M6 BULK | 0.0 | 4.0 | 1.8 | 81.6 | 10.8 | 0.4 | 0.4 | 0.2 | 6.8 |

Of thirty selections made, twenty seven bred true for fatty acid profile. The remaining three selections had different bulk results due either to remnant variability in the original population or due to accidental hybridization made in the M5 generation. Individual plant selections of these selections showed segregation for the new fatty acid type.

Three allelic genes, OL, ol, and ol1, in one locus are the primary genetic determinants of the proportions of the oleic and linoleic acids in safflower. (Knowles and Hill, "Inheritance of Fatty Acid Content in the Seed Oil of a Safflower Introduction from Iran," *Crop Science*, 4:406, 408 1964.). The dominant gene OL codes for a high linoleic acid concentration content of the 75–78% range and an oleic acid content in the 10–15% range in an OL/OL genotype. The ol allele is responsible for the classic oleic level of 64–83% in the ol/ol genotype. A third allele gene, ol1, codes for an oleic acid content in a mid-range of 35–50% in the ol1/ol1 genotype. The genotype of the invention contains a new allelic gene coding for oleic acid, hereby named ol2, which contains 89.5–91.5% oleic acid in the ol2/ol2 genotype (Table 5).

profile of S-901 is then developed using procedures such as those of pedigree breeding. Pedigree plant breeding is a technique used to create new varieties of plants that combine the best qualities of selected existing varieties. The method is limited to self-pollinating species. Parents are selected and artificially crossed. A few of the resulting F1 hybrid seeds are planted and seed from each plant is harvested separately and grown. The genotypic variability becomes apparent in the F2 and the characteristics of each plant are noted. The seed from a small number of promising plants is harvested to grow on to the F3 and the "pedigree" of each plant is recorded. By noting the variability within each of the F3 plants it may be determined which plants of the previous generation depended excessively on heterozygosity for vigor. Selected lines are then grown and bulked.

Backcrossing is a plant breeding technique to introduce a desirable gene into a cultivated variety. The cultivated variety (the recurrent parent) is crossed with the donor parent. The progeny from this cross, which contain 50% of the donor genetic material, are screened for the characteristic and crossed back to the recurrent parent. The progeny of this

TABLE 5

FATTY ACID DISTRIBUTION OF HOMOZYGOUS GENOTYOPES
OL/OL, ol1/ol1, ol/ol, and ol2/ol2

| GENOTYPE | 14:0 | 16:0 | 18:0 | 18:1 | 18:2 | 20:0 | 22:0 | 24:0 | TOT SAT |
|---|---|---|---|---|---|---|---|---|---|
| OL/OL** | 0.1 | 6.3 | 2.5 | 13.9 | 76.0 | 0.4 | 0.2 | 0.1 | 9.6 |
| ol1/ol1* | 0.0 | 4.9 | 2.1 | 52.7 | 38.6 | 0.4 | 0.3 | 0.2 | 8.1 |
| ol/ol (S-518)** | 0.0 | 4.5 | 2.0 | 81.7 | 9.9 | 0.5 | 0.4 | 0.2 | 7.7 |
| ol2/ol2 (S-901)** | 0.0 | 3.8 | 1.8 | 90.3 | 2.3 | 0.4 | 0.4 | 0.2 | 6.6 |

*average of 6 plants
**average of 20 plants

Safflower is primarily self-pollinating, with some cross-pollination. Progeny exhibiting the desired fatty acid profile can be crossed with other progeny to provide a population of safflower seeds having very high oleic acid contents. Further, progeny can be crossed, if desired, with other progeny, or with any other safflower line or cultivar to yield a safflower cultivar having the desired oil content combined with other desired agronomic traits. Any commercial cultivar desired may be employed. Factors such as, for example, seed yield, geographical area, and many others, as is known, will generally dictate the cultivar selected from those available.

S-901 can be crossed onto any superior genotype to create improved cultivars which include the fatty acid profiles characteristic of S-901. A commercially acceptable line with higher oil and fusarium resistance as well as the fatty acid cross, now contain 25% of the genetic material of the donor. The plants are again screened to select plants with the desired trait, and the selected plants backcrossed to the recurrent parent. This process is repeated until little of the genetic material of the donor parent except the desired characteristic exists. The plants are then selfed to produce plants homozygous for the desired trait.

The safflower plant of this invention can be crossed onto genetic sterile lines for use in hybrid breeding and as a simpler way of making crosses than emasculation. Derivatives of this cross can then be crossed onto other lines created using breeding techniques such as, but not limited to, to pedigree breeding. Two parents with superior combining ability that both contain the fatty acid profile of the seed from the safflower plant of this invention can then be intercrossed to create a hybrid with same fatty acid characteristics. In addition, as well as being used for hybrid production, female lines created in this manner can be used in developing new breeding lines without the need of emasculated crosses.

Seeds of line S-901 have been placed on deposit at the America Type Culture Collection (ATCC), Rockville, Md. 20852, USA under deposit accession number ATCC 209181 on Jul. 28, 1997.

Although the invention has been described with respect to a preferred embodiment thereof, it is also to be understood that it is not to be so limited since changes and modifications can be made therein which are within the full intended scope of this invention as defined by the appended claims.

EXAMPLES

Example 1

S-901

M5 plants were grown in breeding cages and yield testing was initiated in order to determine agronomically superior selections in the original population. Analysis of yield and oil characteristics were conducted. Thirteen M5 selections derived from three M4 families were determined to be superior in yield and oil quality characteristics. These lines were bulked to become S-901 and increased for commercial testing.

Example 2

Backcross Onto S-518

S-901 is morphologically distinct from the parental line S-518. In side-by-side comparisons S-901 is shorter and less vigorous looking that S-518. Primary head diameter is less in S-901 than in S-518, it flowers later than S-518 and has a lower oil content than S-518. In yield comparisons, S-901 yields less than S-518 with considerable variation among selections. The selections used to create S-901 yielded 90–95% of the yield of S-518. Table 6 shows the morphological and oil content differences between S-901 and S-518.

TABLE 6

MORPHOLOGICAL AND OIL CONTENT DIFFERENCES BETWEEN S-901 AND S-518

| NO. | HEIGHT (cm) | | PRIMARY HEAD DIAMETER | | ANTHESIS | | OIL CONTENT | |
| --- | --- | --- | --- | --- | --- | --- | --- | --- |
| | S-901 | S-518 | S-901 | S-518 | S-901 | S-518 | S-901 | S-518 |
| 1 | 62 | 70 | 3.0 | 3.6 | 75 | 71 | 41.9 | 44.5 |
| 2 | 67 | 60 | 2.8 | 3.1 | 76 | 71 | 41.9 | 44.7 |
| 3 | 65 | 60 | 2.1 | 2.9 | 74 | 75 | 41.7 | 42.8 |
| 4 | 65 | 65 | 2.8 | 3.0 | 71 | 71 | 41.3 | 44.5 |
| 5 | 65 | 67 | 3.1 | 2.9 | 75 | 72 | 40.6 | 43.3 |
| 6 | 55 | 77 | 3.0 | 3.1 | 74 | 72 | 39.9 | 44.2 |
| 7 | 67 | 65 | 2.9 | 2.8 | 74 | 72 | 41.4 | 44.6 |
| 8 | 65 | 67 | 2.4 | 3.2 | 75 | 73 | 41.5 | 45.4 |
| 9 | 52 | 67 | 2.5 | 3.3 | 75 | 70 | 41.6 | 43.5 |
| 10 | 62 | 67 | 2.9 | 2.7 | 75 | 76 | 40.1 | 44.5 |
| 11 | 55 | 62 | 2.4 | 2.9 | 76 | 71 | 41.5 | 42.9 |
| 12 | 62 | 65 | 2.3 | 2.8 | 73 | 70 | 38.2 | 43.7 |
| 13 | 52 | 72 | 2.6 | 2.5 | 76 | 70 | 40.4 | 43.7 |
| 14 | 62 | 70 | 2.8 | 2.8 | 76 | 72 | 40.3 | 43.3 |
| 15 | 55 | 67 | 2.8 | 3.4 | 74 | 70 | 41.4 | 42.9 |
| 16 | 62 | 67 | 3.0 | 3.5 | 77 | 73 | 41.6 | 44.0 |
| 17 | 70 | 75 | 2.0 | 3.0 | 74 | 74 | 40.7 | 42.6 |
| 18 | 60 | 72 | 2.7 | 3.0 | 79 | 78 | 37.8 | 43.8 |
| 19 | 60 | 70 | 2.6 | 3.5 | 80 | 73 | 37.9 | 41.7 |

TABLE 6-continued

MORPHOLOGICAL AND OIL CONTENT DIFFERENCES BETWEEN S-901 AND S-518

| NO. | HEIGHT (cm) | | PRIMARY HEAD DIAMETER | | ANTHESIS | | OIL CONTENT | |
| --- | --- | --- | --- | --- | --- | --- | --- | --- |
| | S-901 | S-518 | S-901 | S-518 | S-901 | S-518 | S-901 | S-518 |
| 20 | 50 | 65 | 2.7 | | 78 | 73 | 39.2 | 40.9 |
| MEAN | 60.7 | 67.5 | 2.7 | 3.1 | 75.4 | 72.4 | 40.5 | 43.6 |
| STD | 5.53 | 4.33 | 0.3 | 0.3 | 2.0 | 2.1 | 1.3 | 1.1 |
| | t TEST 9.69** | | t TEST 2.44* | | t TEST 4.629** | | t TEST 8.17** | |

Since S-518 served as the source of the mutation leading to S-901 most or all of the differences between the two lines can be removed in one or two cycles of backcrossing, resulting in a line with all of the superior characteristics of S-518 and the fatty acid profile of S-901.

S-518 was emasculated and crossed using pollen from S-901. The F1 seed was grown in a breeding cage. Single F2 seeds were analyzed and the segregation pattern noted (shown in Table 1, infra). F2 plants were grown and plants resembling S-518 morphologically were selected. These plants are screened and those with superior fatty acids selected. F3 plants most similar to S-518 are selected, yield tested and compared to S-518. Additional cycles of backcrossing are done to achieve the result of S-518 with improved fatty acid characteristics. A selection identical to S-518 is then increased for commercial use.

Example 3

S-901 X 6115

S-901 can be crossed onto any superior genotype to create improved cultivars which include the fatty acid profiles characteristic of S-901. Proprietary experimental line 6115 has the normal oleic acid type and has two traits, higher oil content and resistance to Race 4 fusarium, which are lacking in S-901. A selection of S-901 was emasculated and crossed onto 6115. F1 seed was grown under a breeding cage. True crosses were identified by flower color. S-901 has yellow flowers that dry to orange (y/o) while 6115 has flowers that are yellow and dry yellow (y/y). This trait (y/y) is dominant over the yellow/orange (y/o) trait of S-901. F1 plants with y/y flowers were selected. Single seeds of selected plants segregated for fatty acid type as shown in Table 2, infra. F3 plants were selected and screened for fatty acid. Those with the fatty acid profile of S-901 were continued in the breeding program. A commercially acceptable line with higher oil and fusarium resistance as well as the fatty acid profile of S-901 is then developed using procedures such as those of pedigree breeding.

Example 4 d518 X S-901

S-901 can be crossed onto genetic sterile lines for use in hybrid breeding and as a simpler way of making crosses than emasculation. A number of selections of S-901 were crossed onto a fourth backcross of S-518 with a dwarf male sterile characteristic (Weisker, 1994). The F1 of the cross was grown and F2 single seeds analyzed by GC. One selection segregated for the fatty acid profile of S-901. This selection was continued for backcrossing onto S-518. The progeny of this cross are then crossed onto another desirable line using the breeding techniques described in Example 2. Two parents with superior combining ability that both contain the fatty acid profile of S-901 are then intercrossed to create a hybrid with the fatty acid characteristics of S-901.

Example 5

S-901 X FAPOP-14-1-4-2

S-901 can be used as source material for further improvements in fatty acid quality. The fatty acid profile of S-901 segregates uniformly when crossed onto the ol/ol genotype. When crossed onto other genetic backgrounds different genotypes can be expected. Proprietary experimental line FAPOP-14-1-4-2 has a fatty acid profile significantly lower in saturated fatty acids than other safflower lines. It contains 3.2% palmitic acid, 0.9% stearic acid, 69.1% oleic acid, 24.9% linoleic acid, and 0.6% other saturated fatty acids; a total of 4.7% saturated fatty acids. When crossed onto S-901, several beneficial fatty acid profiles are possible. Segregation of different genes between the lines can result in a line with saturated fatty acids below the 4.7% level, further improving the health qualities of the oil. A line with the 4.7% level and oleic acid content higher than 75% can result. The current industry standard for acceptable oleic acid level is 75%. The 69.1% level of FAPOP-14-1-4-2 is, therefore, too low to be acceptable on a commercial level. Table 7 gives the results of twenty single F2 seeds from the cross of S-901 X FAPOP-14-1-4-2. A wide segregation of fatty acid profiles can clearly be seen. Four of the seeds (Nos. 1, 2, 17, 18) demonstrated the possibility of palmitic levels near 2.5%, stearic levels at or under 1.0%, and oleic levels near 90%.

TABLE 7

SINGLE SEED ANALYSIS OF CROSS BETWEEN S-901 AND FAPOP-14-1-4-2

| SEED NO. | 16:0 | 18:0 | 18:1 | 18:2 |
|---|---|---|---|---|
| 1 | 2.3 | 1.0 | 89.6 | 4.8 |
| 2 | 3.1 | 1.7 | 91.3 | 2.1 |
| 3 | 4.2 | 2.0 | 82.4 | 10.0 |
| 4 | 3.7 | 1.4 | 81.1 | 12.5 |
| 5 | 2.9 | 0.9 | 74.6 | 20.0 |
| 6 | 3.1 | 1.4 | 85.7 | 7.6 |
| 7 | 3.3 | 1.3 | 84.4 | 6.3 |
| 8 | 3.7 | 1.6 | 85.3 | 7.2 |
| 9 | 2.4 | 0.9 | 80.4 | 14.6 |
| 10 | 4.1 | 1.5 | 86.5 | 6.4 |
| 11 | 3.1 | 1.9 | 91.3 | 2.1 |
| 12 | 3.4 | 1.8 | 86.3 | 7.0 |
| 13 | 3.1 | 1.0 | 90.8 | 3.3 |
| 14 | 2.6 | 1.4 | 91.5 | 3.2 |
| 15 | 2.9 | 1.1 | 74.8 | 18.7 |
| 16 | 4.1 | 1.9 | 79.6 | 12.8 |
| 17 | 2.2 | 0.9 | 89.1 | 6.6 |
| 18 | 2.2 | 0.5 | 88.2 | 7.4 |
| 19 | 4.4 | 1.7 | 80.1 | 11.7 |
| 20 | 3.0 | 1.2 | 91.0 | 2.5 |

The examples listed above do not limit the type or scope of uses for the invention. Further testing and crossing may create many new types of safflower with different and improved fatty acid profiles for commercial and industrial uses.

What is claimed is:

1. Safflower seeds derived from a safflower line with a gene that controls high levels of oleic acid content of the fatty acid profile in the oil from said seeds, wherein the total unsaturated fatty acid oil content in said seeds is greater than about 92% of the total oil content and wherein the ratio of linoleic acid to oleic acid is less than 0.03 and having ATCC Accession Number 209181.

2. Safflower seeds comprising a fatty acid profile of total unsaturated fatty acids greater than about 92% of the total oil content, wherein the ratio of linoleic acid to oleic acid is less than 0.03 and having ATCC Accession Number 209181.

3. The safflower seeds of claim 2, wherein said total unsaturated fatty acids is greater than about 93% of the total oil content.

4. The safflower seeds of claim 2, wherein said total unsaturated fatty acids is greater than about 94% of the total oil content.

5. Safflower seeds comprising a fatty acid profile which comprises an oleic acid content greater than about 90%, linoleic acid content of about 3% or less, palmitic acid content of less than about 4%, and stearic acid content of about 2.5% or less and having ATCC Accession Number 209181.

6. The safflower seeds of claim 5, wherein said oleic acid content is greater than about 91%, linoleic acid content is less than about 3%, palmitic acid content is less than about 4%, and stearic acid content is less than about 2.5%.

7. A safflower plant having all of the morphological and physiological characteristics of a safflower plant derived from seed designated ATCC Accession Number 209181.

8. A safflower plant that has a trait inherited from safflower line S-901 or a plant derived from safflower line S-901, such that said safflower plant yields bulked seed that provides oil wherein the total unsaturated fatty acid oil content of said seed is greater than about 90% of the total oil content and wherein the ratio of linoleic to oleic acid is less than 0.03 and said safflower line S-901 having ATCC Accession Number 209181.

9. A safflower seed derived from the plant of claim 7.

10. A method of producing seeds with at least about 90% oleic add content from a safflower plant, comprising:

(a) growing a safflower plant having an inheritable trait for oleic acid content of at least about 90% and grown from seed having ATCC Accession Number 209181;

(b) self pollinating the safflower plant of step (a);

(c) cultivating the pollinated safflower plant to produce safflower seeds with an oleic acid content of at least about 90%; and, (d) harvesting the seeds from the plant.

11. A method of producing safflower oil from a safflower seed with an oleic acid content of at least about 90%, comprising the steps of:

(a) growing a safflower plant having an inheritable trait for oleic acid content of at least about 90% and grown from seed having ATCC Accession Number 209181;

(b) self pollinating the safflower plant of step (a);

(c) cultivating the pollinated safflower plant to produce safflower seeds with an oleic acid content of at least about 90%;

(d) harvesting the seeds from the plant; and, (d) producing a safflower oil with an oleic acid content of at least about 90% from the seed.

12. A safflower plant produced from the seed of claim 9.

13. A safflower seed produced from a cross in which one of the parent safflower plants is derived from seed having all of the morphological and physiological characteristics of seed designated ATCC Accession Number 209181.

* * * * *